United States Patent [19]

Yabroff

[11] 4,246,187

[45] Jan. 20, 1981

[54] SEPARATION OF 2,4-TOLYLENE DIISOCYANATE FROM MIXTURES OF 2,4- AND 2,6-TOLYLENE DIISOCYANATE

[75] Inventor: Ronald M. Yabroff, Prospect, Ky.

[73] Assignee: E. I. Du Pont de Nemours and Company, Wilmington, Del.

[21] Appl. No.: 58,154

[22] Filed: Jul. 17, 1979

[51] Int. Cl.$^3$ .......................................... C07C 119/048
[52] U.S. Cl. ............................................. 260/453 SP
[58] Field of Search ................................. 260/453 SP

[56] References Cited

U.S. PATENT DOCUMENTS 3,217,024  11/1965  Park et al. ...................... 260/453 SP
3,591,617   7/1971  Buchsbaum ................... 260/453 SP Primary Examiner—Dolph H. Torrence

[57] ABSTRACT

Separation of 2,4-tolylene diisocyanate from a mixture of 2,4- and 2,6-tolylene diisocyanate by cooling the mixture of isocyanate by passage through a heat exchanger to crystallize a portion of 2,4-tolylene diisocyanate to form a slurry containing no more than about 25% by weight 2,4-tolylene diisocyanate crystals suspended in mother liquor, maintaining the resulting slurry for a nominal residence time of at least about 2 hours at about a constant temperature and centrifuging the slurry to separate 2,4-tolylene diisocyanate crystals from the mother liquor.

6 Claims, 1 Drawing Figure

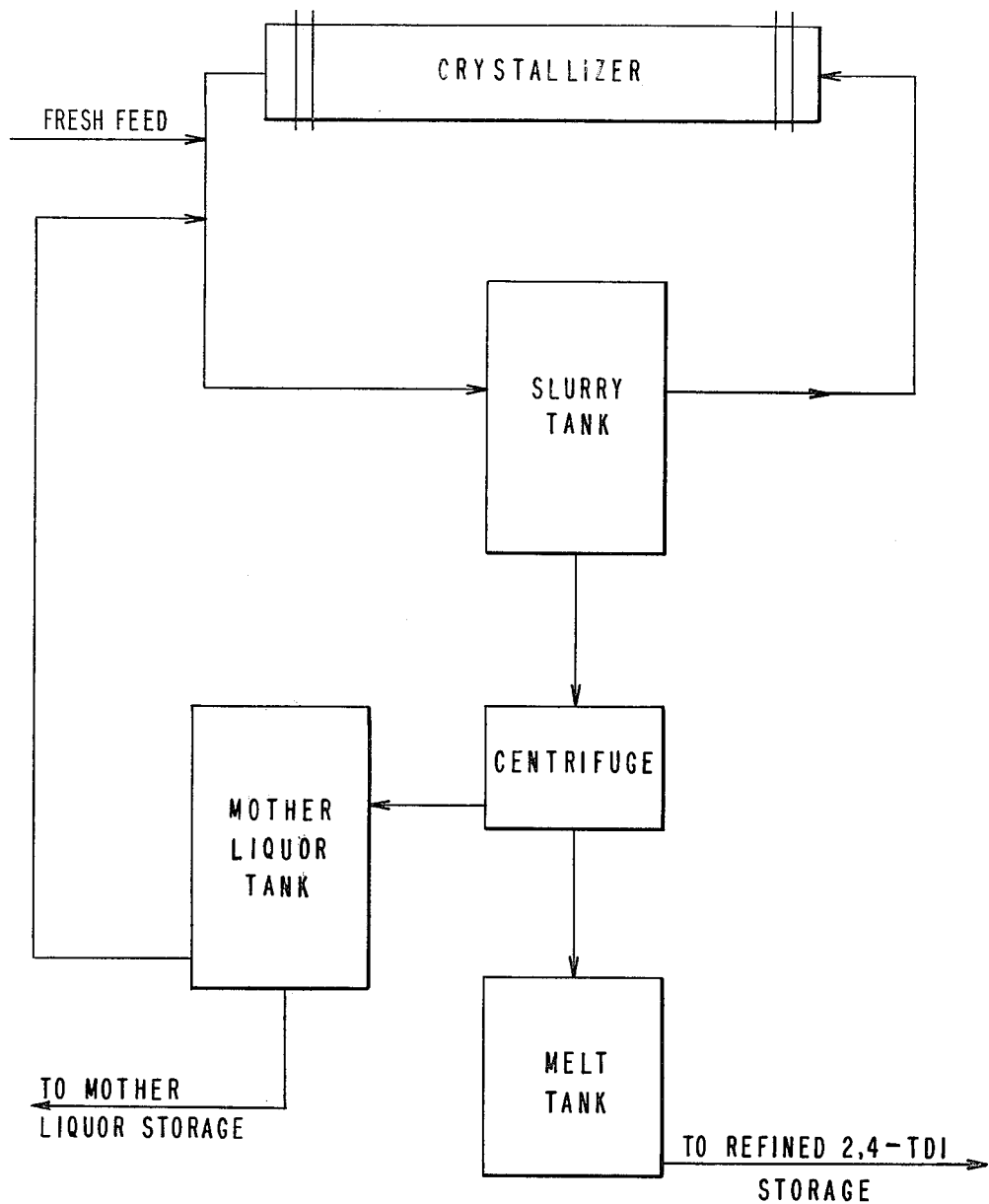

SEPARATION OF 2,4-TOLYLENE DIISOCYANATE FROM MIXTURES OF 2,4- AND 2,6-TOLYLENE DIISOCYANATE

BACKGROUND OF THE INVENTION

The most widely used grade of tolylene diisocyanate (sometimes hereinafter referred to as TDI) for making polyurethanes is a mixture containing about 80 percent 2,4-isomer and 20 percent 2,6-isomer. There is, however, a continuing demand for nearly pure 2,4-tolylene diisocyanate and for an isomer mixture containing about 65 percent 2,4-isomer and 35 percent 2,6-isomer of tolylene diisocyanate. A number of routes are available for the preparation of 2,4-tolylene diisocyanate. These include separation of 2,4-dinitrotoluene from the mixed nitration products of toluene, followed by reduction to the 2,4-diamine and phosgenation. Static crystallization of mixtures of the isomers of tolylene diisocyanate has also been suggested as means of obtaining refined 2,4-tolylene diisocyanate. In particular, U.S. Pat. No. 3,217,024 describes a two-stage static crystallization process which permits the preparation of 2,4-tolylene diisocyanate of acceptable purity. Both of these processes require large expenditures for equipment. The procedure described in U.S. Pat. No. 3,217,024 indicates that partial crystallization of the 2,4-isomer from an agitated mixture of 2,4- and 2,6-tolylene diisocyanate yields a viscous slurry of 2,4-isomer crystals in mother liquor which is difficult to separate by filtration or centrifuging. There is a need in the industry for a relatively inexpensive and simple means for recovering substantially pure 2,4-tolylene diisocyanate from a mixture of its isomers.

SUMMARY OF THE INVENTION

Surprisingly, it has been found that partial crystallization of a mixture of isomers of TDI is an effective and inexpensive method for refining 2,4-tolylene diisocyanate under certain process conditions described hereinafter. More specifically, the present invention is directed to a process for the separation of 2,4-tolylene diisocyanate from a mixture of 2,4- and 2,6-tolylene diisocyanate containing at least about 60% by weight 2,4-tolylene diisocyanate which comprises continuously cooling said mixture of isocyanate by passing the mixture through a scraped-surface heat exchanger to crystallize a portion of the 2,4-tolylene diisocyanate contained in the mixture to form a slurry containing no more than about 25% by weight of crystals of 2,4-tolylene diisocyanate suspended in mother liquor, maintaining the resulting slurry for a nominal residence time of a least about two hours at about a constant temperature to permit crystal growth to occur, and centrifuging slurry to separate and recover 2,4-tolylene diisocyanate crystals from the mother liquor.

DESCRIPTION OF THE PREFERRED EMBODIMENTS

The process of the present invention can be readily described by reference to the flow sheet of the drawing. The crystallizer used in the process is a scraped-surface heat exchanger which is jacketed to permit cooling. By scraped-surface heat exchanger is meant one having means for removing material from its walls, e.g., by spring-loaded blades. In operation, the mixture of 2,4- and 2,6-tolylene diisocyanate is continuously recirculated, from a slurry tank through the crystallizer. The slurry tank is sized so that the slurry formed by crystallization has a nominal residence time of at least 2 hours before being sent to the centrifuge for the separation and recovery of crystals of substantially pure 2,4-tolylene diisocyanate. This minimum residence time is necessary to permit proper growth and digestion of the 2,4-TDI crystals before they are separated by centrifuging. Nominal residence times greater than 2 hours are satisfactory, but residence times of 3 to 4 hours are preferred to provide good separation of the 2,4-tolylene diisocyanate crystals in the centrifuge while at the same time employing a slurry tank of an economically acceptable size. Nominal residence time is calculated by dividing the volume of the slurry by the volume of slurry removed per hour. The pump employed to recirculate the slurry through the crystallizer should be selected to minimize crystal fracture during recirculation. Recessed impeller centrifugal pumps have been found to be well suited for recirculating the crystal slurries formed in this process. In order to prevent settling in the slurry tank, it is desirable to provide low shear agitation, such as that obtained with a low speed propeller or paddle agitator.

The temperature at which the slurry containing 2,4-tolylene diisocyante crystals is maintained in the slurry tank depends on the composition of the mother liquor which is desired. Once the composition of the mother liquor is selected, the temperature of the slurry in the tank can be calculated by the following formula:

$$\%2,4\text{-TDI} = 49.93 + 1.684T(°C.) + 0.02694T^2(°C.),$$

wherein the % 2,4-TDI is the percent by weight of 2,4-TDI in the mother liquor and T represents the temperature at which the slurry is to be maintained in the slurry tank.

For example, a preferred procedure of the present invention is the separation of 2,4-TDI from an 80/20 mixture of 2,4-/2,6-TDI with the simultaneous production of a mother liquor having a 2,4-/2,6-isomer ratio of about 65/35 as this is also a product of commerce. By solving the above equation for T(°C.), the following expression is obtained:

$$T = \frac{-1.684 + \sqrt{-2.5446 + (0.1078)(\% \, 2,4\text{-TDI})}}{0.05388}$$

Setting % 2,4-TDI in the mother liquor equal to 65, T then equals 8.0° C. Thus, to produce a mother liquor containing about 65% 2,4-TDI, the temperature in the slurry tank must be maintained about 8° C. In actual practice, the temperature of the slurry can be maintained about one or two degrees lower because there is a small increase in temperature during the centrifuging step when the surroundings are warmer than the slurry, which is the usual situation. By employing the above expressions, it is obvious that the temperature at which the slurry should be maintained can be calculated for any desired composition of mother liquor. The limits on the useful range of temperature are from about 1° C., the eutectic point of the system, up to about 22° C., the freezing point of 2,4-TDI.

For satisfactory operation of the crystallizer and slurry tank, it is also important that the concentration of 2,4-TDI crystals in the slurry is no more than about 25% by weight, preferably 10-20% by weight, with concentrations of 13-17% being most preferred. At concentrations above 25% by weight, the slurry becomes sufficiently thick that plugging may be encountered. While there are no problems in operating with slurries having a concentration below 10%, operation below 10% solids is not normally economical. The solids concentration of slurry is a function of and can be calculated from the composition of the starting mixture of isomers and the composition of the desired mother liquor. The following expression can be used for this calculation:

% Solids = %2,4-TDI in starting mixture - (% 2,4-TDI in mother liquor)

$$\left( \frac{\% \ 2,6\text{-TDI in starting mixture}}{\% \ 2,6\text{-TDI in mother liquor}} \right)$$

Thus, cooling a 70/30 mixture of 2,4-/2,6-TDI to form a mother liquor containing a 65/35 ratio of 2,4-/2,6-isomers yields a slurry containing 14.3% solids. The previously mentioned preferred separation of 2,4-TDI from an 80/20 mixture of 2,4- and 2,6-isomers with the simultaneous formation of a 65/35 mother liquor yields a slurry having a solids concentration of about 43%. This is far too high to handle in the present process. Therefore, in making the preferred separation, sufficient mother liquor is recirculated to the crystallizer so that the combination of fresh 80/20 mixture and recycled mother liquor provides a feed having an isomer ratio of about 70/30. Thus, in those separations where the slurry concentration would be higher than desired, the slurry concentration can be lowered by recycling a portion of the mother liquor, as indicated in the drawing.

Separation of the crystals of 2,4-TDI from the slurry is accomplished in the present process by centrifuging. The slurry is drawn off or fed to the centrifuge from the slurry tank as shown in the drawing. Either basket or solid bowl type centrifuges may be used, the choice largely depending on the rate of production being considered. For rates on the order of 500 kg/hr of crystals, vertical-basket centrifuges with automatic controls for loading, spinning and discharging are generally preferred. The centrifuge, regardless of its type, should be capable of providing a centrifugal force at least 800 times the force of gravity. In practice, it has been found to be practical to obtain discharged material from centrifuging which contains about 93% by weight of crystalline 2,4-TDI with 7% by weight of mother liquor adhering to the crystals. For the preferred separation previously mentioned with a mother liquor of 65/35 2,4-/2,6-TDI, this results in an overall purity of 97.7% 2,4-TDI when the crystals from the centrifuge are melted to form a uniform liquid. In a basket centrifuge fitted with a 100-mesh screen and providing a force of about 900 times the force of gravity, 900 g's, adequate separations are obtained with centrifuge cake thicknesses of about 4-5 cm with spin times of about 10 minutes. Under most situations encountered, the material being centrifuged will be colder than its surroundings. The slight warming that takes place during spinning is advantageous in that the composition of the mother liquor adhering to the crystals is increased in 2,4-TDI content resulting in a higher purity cake.

The crystals discharged from the centrifuge are dropped to a melt tank as shown in the drawing. The melt tank is maintained at high enough temperature to melt the crystals (25°-40° C.). The melt tank should also be agitated to keep its contents uniform. From the melt tank, the refined 2,4-TDI is normally sent to storage.

The purity of the 2,4-TDI produced by the present process is largely a function of the composition of the mother liquor from which the 2,4-TDI crystals are separated and the extent to which mother liquor is removed from the crystals by centrifuging. As previously indicated, 2,4-TDI of at least 97.5% purity is readily obtained. This is the degree of purity generally accepted commercially for 2,4-TDI. However, this is not the limit of capability for the process because by operating with mother liquor containing a greater proportion of 2,4-TDI and/or raising the efficiency of the centrifuging (increasing spin time, reducing cake thickness, increasing the centrifugal force) much higher purities can be obtained. By starting with TDI containing about 97% 2,4-isomer, 2,4-TDI having a purity exceeding 99.9% can be prepared by the process of this invention.

The following example further illustrates the invention. All parts and percentages are by weight unless stated otherwise.

This example describes the preparation of 2,4-tolylene diisocyanate of 97.5% purity by partial crystallization of an 80/20 mixture of 2,4-/2,6-tolylene diisocyanate. The other product of the separation is a 66.5/33.5 mixture of 2,4-/2,6-tolylene diisocyanate which corresponds to the mother liquor resulting from the partial crystallization of 80/20 isomer mixture.

The equipment employed is arranged substantially as shown in the flow diagram of the drawing. The crystallizer used in this example is a scraped-surface heat exchanger having a length of 2.44 m and a diameter of 0.305 m which provides 2.7 m² of heat transfer surface. The crystallizer is jacketed to permit cooling. The slurry tank is a 1.14 m³ vessel fitted with a low speed propeller agitator. The pump which recirculates slurry from the slurry tank through the crystallizer is a recessed impeller pump which minimizes fracture of the crystals in the slurry. The particular pump is a 2×2×8 inch (5×5×20 cm) pump manufactured by Morris Pumps, Inc., Baldwinsville, N.Y. The centrifuge is a 30-inch (0.76 m) diameter automatic batch basket-type centrifuge with a depth of 15 inches (0.38 m). The centrifuge is capable of 1450 rmp which provides a centrifugal force 900 times the force of gravity. The basket fitted with a 100-mesh screen. The particular centrifuge used is a Model T-300, sold by Sharples-Stokes, Warminster, Pa. The melt tank is a 0.38 m³ vessel fitted with agitation and steam coils. The mother liquor tank is a 0.38 m³ vessel.

To start the system, the crystallizer and the slurry tank are filled with a 70.6/29.4 mixture of 2,4-/2,6-tolylene diisocyanate. The mixture of isocyanate isomers is cooled and partial crystallization of 2,4-tolylene diisocyanate is effected by continuously recycling the isocyanate mixture from the slurry tank through the crystallizer while a liquid coolant at a temperature of about −8° C. is circulated through the jacket of the crystallizer. When the temperature of the slurry which results from partial crystallization of 2,4-isomer reaches 6° C., sufficient slurry is withdrawn from the slurry tank to load the centrifuge. The slurry has a solids content of about 15% by weight. After loading with sufficient slurry to provide a cake thickness of 4.5 cm, the centrifuge automatically enters its spin step to remove the bulk of the mother liquor from the crystals. The spin step extends for 10 minutes. Following the spin step, the centrifuge automatically unloads the crystal cake which consists of about 93% by weight of crystalline 2,4-isomer and 7% mother liquor. The cake from the centrifuge drops into the melt tank. The centrifuge then automatically loads to start the next cycle. The contents of the melt tank are maintained at 30° C. so that the crystals entering the tank are melted to form liquid 2,4-tolylene diisocyanate which has a purity of 97.5%. The centrifuge produces refined 2,4-isomer at a rate of about 76 kg/hr. The volume of the slurry sent to the centrifuge is made up in the slurry tank by the addition of both fresh 80/20 2,4-/2,6-tolylene diisocyanate and a portion of the mother liquor collected from the centrifuge. The purpose for recycling a portion of the mother liquor is to maintain the concentration of 2,4-tolylene diisocyanate crystals at a constant level in the slurry. For the particular set of equipment used in this example, slurry is sent to the centrifuge at a rate of about 471 kg/hr, and its volume is made up in the slurry tank by the addition of 176 kg/hr of 80/20 2,4-/2,6-tolylene diisocyanate which enters at a temperature of 15° C. and 296 kg/hr of mother liquor which is at a temperature of 8° C. The volume of feed per hour is about one-third the volume of the slurry tank so that the nominal residence time is about 3 hours.

I claim:

1. A process for the separation of 2,4-tolylene diisocyanate from a mixture of 2,4- and 2,6-tolylene diisocyanate containing at least about 60% by weight 2,4-tolylene diisocyanate which comprises continuously cooling said mixture of isocyanate by passing the mixture through a scraped-surface heat exchanger to crystallize a portion of the 2,4-tolylene diisocyanate contained in the mixture to form a slurry containing no more than about 25% by weight of crystals of 2,4-tolylene diisocyanate suspended in mother liquor, maintaining the resulting slurry for a nominal residence time of at least about 2 hours at about a constant temperature to permit crystal growth to occur, and centrifuging slurry to separate 2,4-tolylene diisocyanate crystals from the mother liquor.

2. A process of claim 1 wherein the nominal residence time is about 3-4 hours.

3. A process of claim 1 wherein the slurry contains from about 10-20% by weight of crystals of 2,4-tolylene diisocyanate.

4. A process of claim 1 wherein a portion of the mother liquor is recirculated to the slurry to maintain the concentration of 2,4-tolylene diisocyanate crystal at about 10-20% by weight.

5. A process of claim 4 wherein the mixture of isomers of tolylene diisocyanate to be separated contains about 77-83% by weight 2,4-tolylene diisocyanate and about 17-23% by weight 2,6-tolylene diisocyanate.

6. A process of claim 1 wherein th constant temperature of the slurry is calculated from the formula:

$$\%2,4\text{-TDI} = 49.93 + 1.684T\ (°C.) + 0.02694T^2(°C.)$$

wherein the % 2,4-TDI is the percent 2,4-tolylene diisocyanate in the mother liquor and T represents the temperature of the slurry.

* * * * *